US006261838B1

(12) United States Patent
Cone et al.

(10) Patent No.: US 6,261,838 B1
(45) Date of Patent: Jul. 17, 2001

(54) RAT MELANOCORTIN RECEPTOR MC3-R

(75) Inventors: Roger D. Cone, Oregon City; Linda Roselli-Rehfuss, Portland; Kathleen G. Mountjoy, Portland; Linda S. Robbins, Portland, all of OR (US)

(73) Assignee: Oregon Health Science University, Portland, OR (US)

( * ) Notice: Subject to any disclaimer, the term of this patent is extended or adjusted under 35 U.S.C. 154(b) by 0 days.

(21) Appl. No.: 09/191,359

(22) Filed: Nov. 13, 1998

Related U.S. Application Data

(62) Division of application No. 08/044,812, filed on Apr. 8, 1993, now Pat. No. 5,837,521.

(51) Int. Cl.[7] .............................. C07K 14/705; C12N 5/10
(52) U.S. Cl. ..................... 435/325; 435/361; 435/252.3; 530/350
(58) Field of Search ..................................... 530/350, 395, 530/399; 435/69.1, 325, 361, 252.3; 536/23.5

(56) References Cited

U.S. PATENT DOCUMENTS

| 4,683,195 | 7/1987 | Mullis et al. . |
|---|---|---|
| 5,280,112 | 1/1994 | Cone et al. . |
| 5,532,347 | 7/1996 | Cone et al. . |
| B1 4,683,202 | 11/1990 | Mullis . |

FOREIGN PATENT DOCUMENTS

| WO 93 21315 | 10/1993 | (WO) . |
| WO 93 21316 | 10/1993 | (WO) . |

OTHER PUBLICATIONS

Ahmed et al., "Isolation and partial purification of a melanocyte–stimulating hormone receptor from B16 murine melanoma cells. A novel approach using a cleavable biotinylated photoactivated ligand and streptavidin–coated magnetic beads,"*The Biochemical Journal* 286:377–382 (Sep. 1, 1992).
Bergendahl et al., "Short–Term Starvation Decreases POMC mRNA but Does Not Alter GnRH mRNA in the Brain of Adult Male Rats," *Neuroendocrinol.* 56:913–920 (1992).
Bertling, "Transfection of a DNA/Protein Complex into Nuclei of Mammalian Cells Using Polyoma Capsids and Electroporation," *Bioscience Reports* 7:107–112 (1987).
Bost et al., "Molecular characterization of a corticotropin receptor," *Molecular and Cellular Endocrinology* 44:1–9 (1986).
Bost et al., "Similarity between the corticotropin (ACTH) receptor and a peptide encoded by an RNA that is complementary to ACTH mRNA," *PNAS* 82:1372–1375 (Mar. 1985).
Brady et al., "Altered Expression of Hypothalamic Neuropeptide mRNAs in Food–Restricted and Food–Deprived Rats," *Neuroendocrinol.* 52:441–447 (1990).

Buckley & Ramachandran, "Characterization of corticotropin receptors on adrenocortical cells," *Proc. Natl. Acad. Sci. USA* 78:7431–7435 (1981).
Chen & Okayama, "High–Efficiency Transformation of Mammalian Cells by Plasmid DNA," *Mol. Cell. Biol.* 7:2745–2752 (1987).
Chen et al., "A Colorimetric Assay for Measuring Activation of $G_s$– and $G_q$–Coupled Signaling Pathways," *Analyt. Biochem.* 226:349–354 (1995).
Chhajlani et al., "Molecular cloning and expression of the human melanocyte stimulating hormone receptor cDNA," *FEBS Letters* 309(3):417–420 (Sep. 14, 1992).
Chirgwin et al., "Isolation of Biologially Active Ribonucleic Acid for Sources Enriched in Ribonuclease," *Biochemistry* 18:5294–5299 (1979).
DeWied & Jolles, "Neuropeptides derived from pro–opiocortin: Behavorial, physiological and neurochemical effects," *Physiol. Rev.* 62:976–1059 (1982).
Dixon et al., "Structural features required for ligand binding to the β–adrenergic receptor," *EMBO J.* 6:3269–3275 (1987).
Eberle et al., "Receptor–specific antibodies by immunization with 'antisense' peptides?," *Peptide Research* 2(3):213–220 (1989).
Felgner et al., "Enhanced Gene Delivery and Mechanism Studies with a Novel Series of Cationic Lipid Formulations," *J. Biol. Chem.* 269:2550–2561 (1994).
Fink et al., "The CGTCA sequence motif is essential for biological activity of the vasoactive intestinal peptide gene cAMP–regulated enhancer," *Proc. Natl. Acad. Sci. USA* 85:6662–6666 (1988).
Gantz et al., "Molecular Cloning of a Novel Melanocortin Receptor," *J. Biol. Chem.* 268:8246–8250 (1993).
Gerst et al., "Dual Regulation of β–Melanotropin Receptor Function and Adenylate Cyclase by Calcium and Guanosine Nucleotides in the M2r Melanoma Cell Line," *Mol. Pharmacol.* 31:81–88 (1987).

(List continued on next page.)

Primary Examiner—Lorraine Spector
(74) Attorney, Agent, or Firm—McDonnell Boehnen Hulbert & Berghoff

(57) ABSTRACT

The present invention relates to a mammalian melanocortin receptor. The invention is directed toward the isolation, characterization and pharmacological use of a mammalian melanocortin receptor (MC3-R). The invention specifically provides a particular melanocortin receptor, termed MC3-R, isolated as a complementary DNA copy of mRNA corresponding to the gene for this receptor in rats. Also provided is a eukaryotic recombinant expression construct capable of expressing a mammalian melanocortin receptor in cultures of transformed eukaryotic cells and such cultures of transformed eukaryotic cells that synthesize a mammalian melanocortin receptor. The invention also provides methods for screening in vitro agonists and antagonists of such a melanocortin receptor using preparations of receptor protein from such cultures of eukaryotic cells transformed with a recombinant expression construct.

2 Claims, 9 Drawing Sheets

OTHER PUBLICATIONS

Gilman, "A Protein Binding Assay for Adenosine 3':5'-Cyclic Monophosphate," *Proc. Natl. Acad. Sci. USA* 67:305–312 (1979).

Grahame–Smith et al., "Adenosine3':5'-Monophosphate as the Intracellular Mediator of the Action of Adrenocorticotropic Hormone on the Adrenal Cortex," *J. Biol. Chem.* 242:5535–5541 (1967).

Gruber & Callahan, "ACTH–(4–10) through gamma–MSH: evidence for a new class of central autonomic nervous system–regulating peptides," *Am. Physiol. Soc.* 257:R681–R694 (1989).

Hanneman et al., "Peptides encoded by the pro–opiomelanocortin gene," in *Peptide Hormone as Prohormones*, G. Martinez, ed. (Ellis Horwood Ltd.: Chichester, UK) pp. 53–82 (1987).

Hofmann et al., "Radioactive probes for adrenocorticotropic hormone receptors," *Biochemistry* 25(6):1339–1346 (Mar. 25, 1986).

Hruby et al., "Cyclic Lactam α–Melanotropin Analogues of Ac–Nle$^4$–cyclo[Asp$^5$, D–Phe$^7$,Lys$^{10}$] α–Melanocyte–Stimulating Hormone–(4–10)–NH$_2$ with Bulky Aromatic Amino Acids at Position 7 Show High Antagonist Potency and Selectivity at Specific Melanocortin Receptors," *J. Med. Chem.* 38:3454–3461 (1995).

Kameyama et al., "Expression of melanocyte stimulating hormone receptors correlates with mammalian pigmentation, and can be modulated by interferons," *J. Cellular Physiology* 137(1):35–44 (Oct. 1988).

Karnik et al., "Cysteine residues 110 and 187 are essential for the formation of correct structure in bovine rhodopsin," *Proc. Natl. Acad. Sci. USA* 85:8459–8463 (1988).

Klein et al., "Pressor and cardioaccelerator effects of gamma MSH and related peptides," *Life Sci.* 36:769–775 (1985).

Labbe et al., "Molecular Cloning of a Mouse Melanocortin 5 Receptor Gene Widley Expressed in Peripheral Tissues," *Biochem.* 33:4543–4549 (1994).

Laursen and Belknap, "Intracerebroventricular Injections in Mice," *J. Pharmacol. Methods* 16:355–357 (1986).

Leiba et al., "The melanocortin receptor in the rat lacrimal gland: a model system for the study of MSH (melanocyte stimulating hormone) as a potential neurotransmitter," *European Journal of Pharmacology* 181(1–2):71–82 (May 31, 1990).

Libert et al., "Selective Amplification and Cloning of Four New Members of the G Protein–Coupled Receptor Family," *Science* 244:569 (1989).

Lin et al., "A γmelanocyte stimulating hormone–like peptide causes reflex natriuresis after acute unilaterasl nephrectomy," *Hypertension* 10:619–627 (1987).

Ling et al., "Synthesis and biological activity of four gamma–melanotropin peptides derived from the cryptic region of the adrenocorticotropin/β–lipotropin precursor," *Life Sci.* 25:1773–1780 (1979).

Lu et al., "Agouti protein is an antagonist of the melanocyte–stimulating–hormone receptor," *Nature* 371:799–802 (1994).

Masu et al., "cDNA cloning of bovine substance–K receptor through oocyte–expression system," *Nature* 329:836–838 (1987).

Matsuda et al., "Structure of a cannabinoid receptor and functional expression of the cloned cDNA," *Nature,* 346:561–564 (1990).

Mertz et al., "Adrenocorticotropin receptors: Functional expression from rat adrenal mRNA in *Xenopus laevis* oocytes," *PNAS* 88:8525–8529 (1991).

Moore et al., *Endocrinology* 34:107–114 (1991).

Mountjoy et al., "Localization of the Melanocortin–4 Receptor (MC4–R) in Neuroendocrine and Autonomic Control Circuits in the Brain," *Mole. Endocrinol.* 8:1298–1308 (1994).

Mountjoy et al., "The cloning of a family of genes that encode the melanocortin receptors," *Science* 257:1248–1251 (1992).

Oelofsen & Ramachandran, "Studies of Corticotropin Receptors on Rat Adipocytes," *Arch. Biochem. Biophys.* 225:414–421 (1983).

Oki et al., "γ–MSH Fragments from ACTH–β–LPH Precursor Have an Affinity for Opiate Receptors," *Eur. J. Pharmacol.* 64:161–164 (1980).

Pawalek, "Studies on the Cloudman Melanoma Cell Line as a Model for the Action of MSH," *Yale J. Biol. Med.* 58:571–578 (1985).

Pawelek, "Factor Regulating Growth and Pigmentation of Melanoma Cells," *J. Invest. Dermatol.* 66:201–209 (1976).

Roselli–Rehfuss et al., "Identification of a receptor for γ melanotropin and other proopiomelanocortin peptides in the hypothalamus and limbic system," *Proc. Natl. Acad. Sci. USA* 90:8856–8860 (1993).

Saiki et al., "Primer–Directed Enzymatic Amplificaiton of DNA with a Thermostable DNA Polymerase," *Science* 239:487–491 (1988).

Sambrook et al., 1990, *Molecular Cloning: A Laboratory Manual* (Cold Spring Harbor Press: New York).

Sanger et al., "DNA sequencing with chain–terminating inhibitors," *Proc. Natl. Acad. Sci. USA* 74:5463–5467 (1977).

Schild, "pA, A New Scale for the Measurement of Drug Antagonism," *Brit J. Pharmacol.* 2:189–206 (1947).

Schimmer et al., "Adrenocorticotropin–Resistant Mutants of the Y1 Adrenal Cell Line Fail to Express the Adrenocorticotropin Receptor," *J. Cell Physiol.* 163:164–171 (1995).

Schimuze, "Thirty–five years of progress in the study of MSH," *Yale J. Biol. Med.* 58:561–570 (1985).

Shimizu et al., "Effects of MSH on Food Intake, Body Weight and Coat Color of the Yellow Obese Mouse," *Life Sci.* 45:543–552 (1989).

Siegrist et al., "Characterization of Receptors for α–Melanocyte–stimulating Hormone on Human Melanoma Cells," *Cancer Research* 49:6352–6358 (Nov. 15, 1989).

Siegrist et al., "Quantification of MSH receptors on mouse melanoma tissue by receptor autoradiography," *J. Receptor Res.* 11:323–331 (1991).

Slominski et al., "Melanotropic activity of gamma NSH peptides in melanoma cells," *Life Sci.* 50:1103–1108 (1992).

Smithies et al., "Insertion of DNA sequences into the human chromosomal β–globin locus by homologous recombination," *Nature* 317:230–234 (1985).

Solca et al., "The receptor for α–melanotropin of mouse and human melanoma cells," *J. Biol. Chem.* 264:14277–14280 (1989).

Spindel et al., "Cloning and Functional Characterization of a Complementary DNA Encoding the Murine Fibroblast Bobmesin/Gastrin–Releasing Peptide Receptor," *Mol. Endocrinol.* 4:1956–1963 (1990).

Tatro & Reichlin, "Specific receptors for α–melanocyte–stimulating hormone are widely distributed in tissues of rodents," *Endocrinology* 121:1900–1907 (1987).

Tatro et al., "Melanotropin Receptors of Murine Melanoma Characterized in Cultured Cells and Demonstrated in Experimental Tumors in Situ," *Cancer Res.* 50:1237–1242 (1990).

Thomas & Capecchi, "Site–Directed Mutagenesis by Gene Targeting in Mouse Embryo–Derived Stem Cells," *Cell* 51:530–512 (1987).

*Tissue Culture,* Academic Press, Kruse & Patterson, editors (1973).

Tsujii et al., "Acetylation Alters the Feeding Response to MSH and Beta–Endorphin," *Brain Res. Bull.* 23:165–169 (1989).

Yen et al., "Obesity, diabetes, and neoplasia in yellow $A^{vy}$/–mice: ectopic expression of the agouti gene," *FASEB J.* 8:479–488 (1994).

Zhou et al., "Cloning and expression of human and rat $D_1$ dopamine receptors," *Nature* 347:76–80 (Sep. 1990).-

FIG. 1A

```
                     GGCTGTAACTGTAGCAACCGGTGTTGGGTGGGATGAGAAGAGACCAGA
GAGAGAGAGGGTCAGAGCGACAGGGATGAGACAGGCTGGTCAGAGTCTGCACTGATTGTTGGAGACGCAA
AGGAAAGTTTTTCTATGTCTCCAACCTCCCCCCTCCCCCGTTTCTCTCTGGAGAAACTAAAATCTAGA
CTGGACAGCATCCACAAGAGAAGCACCTAGAAGAAGATTTTTTTTCCCAGCAGCTTGCTCAGGACCCTGC
```

| | | | | | | | | | | | | | | | | |
|---|---|---|---|---|---|---|---|---|---|---|---|---|---|---|---|---|
| AGGAGCTGCAGCCGGAACTGGTCCCGCCGATAACC | ATG | AAC | TCT | TCC | TGC | TGC | CCG | TCC | TCC | | | | | | | |
| | | Met | Asn | Ser | Ser | Cys | Cys | Pro | Ser | Ser | | | | | | |
| | | | | | | | | | | | | | | | | 379 |
| TCT | TAT | CCG | ACG | CTG | CCT | AAC | CTC | TCC | CAG | CAC | CCT | GCA | GCC | CCC | TCT | GCC | AGC |
| Ser | Tyr | Pro | Thr | Leu | Pro | Asn | Leu | Ser | Gln | His | Pro | Ala | Ala | Pro | Ser | Ala | Ser |
| | | | | | | | | | | | | | | | | 433 |
| ACC | CGG | AGT | GGC | AGT | GGG | TTC | TGC | GAG | CAG | GTT | TTC | ATC | AAG | CCA | GAG | CTC | TTC |
| Asn | Arg | Ser | Gly | Ser | Gly | Phe | Cys | Glu | Gln | Val | Phe | Ile | Lys | Pro | Glu | Val | Phe |
| | | | | | | | | | | | | | | | | 487 |
| CTG | GCA | CTG | GGC | ATC | GTC | AGT | CTG | ATG | GAA | AAC | ATC | CTG | GTG | ATC | CTG | GCT | GTG |
| Leu | Ala | Leu | Gly | Ile | Val | Ser | Leu | Met | Glu | Asn | Ile | Leu | Val | Ile | Leu | Ala | Val |
| | | | | | | | | | | | | | | | | 541 |
| GTG | AGG | AAC | GGC | AAC | CTG | CAC | TCC | CCC | ATG | TAC | TTC | TTC | CTG | CTG | AGC | CTG | GTG |
| Val | Arg | Asn | Gly | Asn | Leu | His | Ser | Pro | Met | Tyr | Phe | Phe | Leu | Leu | Ser | Leu | Leu |
| | | | | | | | | | | | | | | | | 595 |
| CAG | GCC | GAC | ATG | CTG | GTG | AGC | CTG | TCC | AAC | TCC | CTG | GAG | ACC | ATC | ATG | ATC | GTG |
| Gln | Ala | Asp | Met | Leu | Val | Ser | Leu | Ser | Asn | Ser | Leu | Glu | Thr | Ile | Met | Ile | Val |

FIG. 1B

```
                                                                                                    649
GTT ATC AAC AGC GAC TCC CTG ACC TTG GAG GAC CAA TTC ATC CAG CAC ATG GAC
Val Ile Asn Ser Asp Ser Leu Thr Leu Glu Asp Gln Phe Ile Gln His Met Asp 703
    622
AAC ATC TTC GAC TCT ATG ATC TGC TCC CTG GTG GCC TCC ATC TGC AAC CTC
Asn Ile Phe Asp Ser Met Ile Cys Ser Leu Val Ala Ser Ile Cys Asn Leu 757
    676
CTG GCC ATC GCC GTG GAC AGG TAC GTC ACC ATC TTC TAT GCC CTC CGT TAC CAC
Leu Ala Ile Ala Val Asp Arg Tyr Val Thr Ile Phe Tyr Ala Leu Arg Tyr His 811
    730
AGC ATG ACG GTT AGG AAA GCC CTC TCC TTG ATC GTG GCC ATC TGG GTC TGC
Ser Ile Met Thr Val Arg Lys Ala Leu Ser Leu Ile Val Ala Ile Trp Val Cys 865
    784
TGT GGC ATC TGC GGC GTG ATG TTC ATC GTC TAC TCC GAG AGC AAG ATG GTC ATC
Cys Gly Ile Cys Gly Val Met Phe Ile Val Tyr Ser Glu Ser Lys Met Val Ile 919
    838
GTG TGC CTC ATC ACC ATG TTC TTC GCC ATG GTG CTC CTC ATG GGC ACC CTG TAC
Val Cys Leu Ile Thr Met Phe Phe Ala Met Val Leu Leu Met Gly Thr Leu Tyr 973
    892
ATC CAC ATG TTC CTC TTC GCC AGG CTG CAC GTC CAG CGC ATC GCG GCA CTG CCA
Ile His Met Phe Leu Phe Ala Arg Leu His Val Gln Arg Ile Ala Ala Leu Pro

```
                                                                                  1027
CCT GCT GAC GGG GTA GCC CCG CAG CAG CAC TCG TGC ATG AAG GGG GCC GTC ACC
Pro Ala Asp Gly Val Ala Pro Gln Gln His Ser Cys Met Lys Gly Ala Val Thr
                                                                                  1081
ATC ACC ATC CTG CTG GGG GTT TTC ATC TTC TGC TGG GCG CCT TTC TTC CTC CAC
Ile Thr Ile Leu Leu Gly Val Phe Ile Phe Cys Trp Ala Pro Phe Phe Leu His
                                                                                  1135
CTG GTC CTC ATC ATC ACC TGC CCC ACC AAC CCC TAC TGC ATC TGC TAC ACG GCG
Leu Val Leu Ile Ile Thr Cys Pro Thr Asn Pro Tyr Cys Ile Cys Tyr Thr Ala
                                                                                  1189
CAC TTC AAC ACC TAC CTG GTT CTC ATC ATG TGC AAC TCT GTC ATC GAC CCC CTC
His Phe Asn Thr Tyr Leu Val Leu Ile Met Cys Asn Ser Val Ile Asp Pro Leu
                                                                                  1243
ATC TAC GCC TTC CGC AGC CTG GAG CTG CGA AAC ACC TTC AAG GAG ATT CTC TGC
Ile Tyr Ala Phe Arg Ser Leu Glu Leu Arg Asn Thr Phe Lys Glu Ile Leu Cys
                                                                                  1297
GGT TGC AAT GGC ATG AAC GTG GGC TAG GAACCCCCGAGGAGGTGTTCCACGGCTAGCCAAGA
Gly Cys Asn Gly Met Asn Val Gly

GAGAAAGCAATGCTCAGGTGAGACACAGAAGGG
```

FIG. 2A

```
                I
rMC3-R    1  MnsccpsssyptlpnlsqhpaapsasnrsgsgfCeqVfIkpevFLaLGivSLmENiLVil
hMSH-R    1  MavQgsQrrLLGSLNStptAipqlGLAaNQtgarCLeVSIsDGLFLSLGLVSLVENaLVVa
mMSH-R    1  MstQepQksLLGSLNS--nAtshLGLATNQsEpwCLyVSIPDGLFLSLGIVSLVENvLVVi
hACTH-R   1                                  MKHIiNsYENInnTARNNSDCPrVvLPEEIFFTiSIVGVLENLiVLL
bACTH-R   1                                  MKHInlYENINsTARNNSDCPaVilPEEIFFTvSIVGVLENLmVLL II
rMC3-R   62  avvrNgNLHSPMYfFllsLlqaDmLVSlsNsLETimIvvinsdsLtledqfiQhmDNifDs
hMSH-R   62  tIaKNRNLHSPMYcFICCLALSDLLVSgtNVLETavILLLEaGaLVARaAvLQQLDNvIDV
mMSH-R   60  AItKNRNLHcPMYyFICCLALSDLmVSvsiVLETtiILLLEvGiLVARvAlvQQLDNlIDV
hACTH-R  48  AVfKNKNLQaPMYFFICSLAISDMLGSLYKILENiLIiLrNMGYLkPRGSFEtTADDiIDS
bACTH-R  48  AVaKNKsLQsPMYFFICSLAISDMLGSLYKILENvLImfkNMGYLePRGSFEsTADDvvDS
```

FIG. 2B

```
                    III                                                    IV
rMC3 - R    123  miCiSlvaSiCnLLAIAVDRYvtIFYALRYHSImTvrkAlslivAIWVccgicgvmFIvYs
                 |||||||||||||||||||||||||||||||||||||||||||||||||||||||||||||
hMSH - R    123  itCsSMlSSLCFLGAIAVDRYISIFYALRYHSIVTLPRApRAVaAIWVaSvVfSTLFIaYY
                 |||||||||||||||||||||||||||||||||||||||||||||||||||||||||||||
mMSH - R    121  LiCgSMvSSLCFLGiIAiDRYISIFYALRYHSIVTLPRARRAVvgIWmvSiVsSTLFItYY
                 |||||||||||||||||||||||||||||||||||||||||||||||||||||||||||||
hACTH - R   109  LFvLSLLGSIfSLSVIAADRYITIFHALRYHSIVTmrRtvvvLTVIWtfCTGtGITmviFS
                 |||||||||||||||||||||||||||||||||||||||||||||||||||||||||||||
bACTH - R   109  LFvLSLLGSIfSLSVIAADRYITIFHALqYHrImTpapcprhLTVlWagCTGsGITiVtFS V
rMC3 - R    184  eskmVivCLitmFfAMvlLMgtLYiHMflfArlHvQrIAaLppadgvapQQhscmKGAVTi
                 |||||||||||||||||||||||||||||||||||||||||||||||||||||||||||||
hMSH - R    184  dHvAVLLCLVvFFLAMLvLMAvLYvHMlaRAcqHaQgIArLHKRqRpvhQGF-gLKGAVTL
                 |||||||||||||||||||||||||||||||||||||||||||||||||||||||||||||
mMSH - R    182  kHtAVLLCLVtFFLAMLaLMAiLYaHMFtesvpARvsIAqLHKRrRsirQGF-cLKGAaTL
                 |||||||||||||||||||||||||||||||||||||||||||||||||||||||||||||
hACTH - R   170  HHVPTVItFTsLFPLMLvFILCLYVHMF    SHTRkistLPrAN-MKGAiTL
                 |||||||||||||||||||||||||||||||||||||||||||||||||||||||||||||
bACTH - R   170  HHVPTVIaFTaLFPLMLaFILCLYVHMF    SHTRrtpslLPkAN-MrGAVTL
```

FIG. 2C

```
                         VI                                                    VII rMC3-R   245 TILLGvFifCWaPFFLHLvLIitCPtnPyCiCytahFNtyLvLImCNsvIDPLIYAFrSlE
hMSH-R   244 TILLGIFFLCWGPFFLHLtLIVLCPeHPTCgCIFKNFNLFLaLIiCNaiIDPLIYAFhSQE
mMSH-R   242 TILLGIFFLCWGPFFLHLLLIVLCPqHPTCsCIFKNFNLFLlLIvlsstvDPLIYAFRSQE
hACTH-R  222 TILLGVFIFCWAPFVLHVLLMTFCPsnPYCACYMSLFQVNGmLIMCNAvIDPFIYAFRSPE
bACTH-R  222 TvLLGVFIFCWAPFVLHVLLMTFCPadPYCACYMSLFQVNGvLIMCNAiIDPFIYAFRSPE rMC3-R   306 LRnTfKEiLcgcngmnvg  323
hMSH-R   305 LRrTLKEVLtCS--W     317
mMSH-R   303 LRmTLKEVLlCS--W     315
hACTH-R  283 LRdAFKKMifCSrYW     297
bACTH-R  283 LRvAFKKMviCncYq     297
```

RAT MELANOCORTIN RECEPTOR MC3-R

This application is a divisional of U.S. Ser. No. 08/044,812, filed Apr. 8, 1993, now U.S. Pat. No. 5,837,521, issued Nov. 17, 1998. +gi This invention was made with government support under R29DK41921, R01DK43859 and P01DK44239 by the National Institutes of Health. The government has certain rights in the invention.

BACKGROUND OF THE INVENTION

1. Field of the Invention

This invention relates to melanocortin receptors from mammalian species and the genes corresponding to such receptors. Specifically, the invention relates to the isolation, cloning and sequencing of a complementary DNA copy of the messenger RNA (mRNA) of a novel rat melanocortin receptor gene responsive to γ-melanocyte stimulating hormone, α-melanocyte stimulating hormone and adrenocorticotropic hormone. This receptor has been termed the melanocortin-3 receptor (MC3-R). The invention relates to the construction of eukaryotic recombinant expression constructs capable of expressing MC3-R in cultures of transformed eukaryotic cells, and the production of MC3-R in such cultures. The invention relates to the use of such cultures of transformed eukaryotic cells to produce homogeneous compositions of MC3-R protein. The invention also provides cultures of such cells producing MC3-R for the characterization of novel and useful drugs. Antibodies against and epitopes of MC3-R protein are also provided by the invention.

2. Background of the Invention

The proopiomelanocortin (POMC) gene product is processed to produce a large number of biologically active peptides. Two of these peptides, α-melanocyte stimulating hormone (αMSH), and adrenocorticotropic hormone (ACTH) have well understood roles in control of melanocyte and adrenocortical function, respectively. Both of these hormones, however, are found in a variety of forms with unknown functions, one of which is γ-melanocyte stimulating hormone (γMSH). Unlike αMSH or βMSH, γMSH has little or no ability to stimulate pigmentation (Ling et al., 1979, Life Sci. 25: 1773–1780; Slominski et al., 1992, Life Sci. 50: 1103–1108). However, γMSH has been shown to have potent pressor, cardioaccelerator and natriuretic actions and acts both in the central nervous system and at the renal afferent nerve (Gruber & Callahan, 1989, Am. Physiol. Soc. 257: R681–R694; Klein et al., 1985, Life Sci. 36: 769–775; Lin et al., 1987, Hypertension 10: 619–627).

The melanocortin peptides also have a diverse array of biological activities in other tissues, including the brain and immune system, and bind to specific receptors in these tissues with a distinct pharmacology [see, Hanneman et al., in *Peptide Hormone as Prohormones*, G. Martinez, ed. (Ellis Horwood Ltd.: Chichester, UK) pp. 53–82; DeWied & Jolles, 1982, Physiol. Rev. 62: 976–1059 for reviews].

A complete understanding of these peptides and their diverse biological activities requires the isolation and characterization of their corresponding receptors. Some biochemical studies have been reported in the prior art.

Shimuze, 1985, Yale J. Biol. Med. 58: 561–570 discusses the physiology of melanocyte stimulating hormone.

Tatro & Reichlin, 1987, Endocrinology 121: 1900–1907 disclose that MSH receptors are widely distributed in rodent tissues.

Solca et al., 1989, J. Biol. Chem. 264: 14277–14280 disclose the molecular weight characterization of mouse and human MSH receptors linked to radioactively and photoaffinity labeled MSH analogues.

Siegrist et al., 1991, J. Receptor Res. 11: 323–331 disclose the quantification of receptors on mouse melanoma tissue by receptor autoradiography.

Cone & Mountjoy, U.S. patent application Ser. No. 07/866,979, filed Apr. 10, 1992, disclose the isolation of human and mouse α-MSH receptor genes and uses thereof (incorporated herein by reference).

Cone & Mountjoy, U.S. patent application Ser. No. 07/866,560, filed Apr. 10, 1992, disclose the isolation of human and bovine ACTH receptor genes and uses thereof (incorporated herein by reference).

Mountjoy et al., 1992, Science 257: 1248–1251 disclose the isolation of cDNAs encoding mammalian ACTH and MSH receptor proteins.

The present invention comprises a nucleic acid comprising a complementary DNA (cDNA) copy of the mRNA of a rat MC3-R gene responsive to γ-melanocyte stimulating hormone. The invention also encompasses the nucleotide sequence of this gene and the deduced amino acid sequence of its cognate protein, a homogeneous composition of the melanocortin-3 receptor (MC3-R), nucleic acid hybridization probes and a method for determining the tissue distribution of expression of the gene, a recombinant expression construct capable of expressing the gene in cultures of transformed eukaryotic cells, and such cultures of transformed eukaryotic cells useful in the characterization of novel and useful drugs.

DESCRIPTION OF THE DRAWINGS

FIGS. 1A–1C illustrates the nucleotide (SEQ ID No:3) and amino acid (SEQ ID No.:4) sequences of the rat melanocortin-3 receptor.

FIGS. 2A–2C presents an amino acid sequence comparison between the rat melanocortin-3 receptor (MC3-R) protein and the human and mouse melanocyte stimulating hormone receptor protein (MSH$^R$) and the human and bovine adenocorticotropin receptor (ACTH$^R$).

SUMMARY OF THE INVENTION

Figure 3:
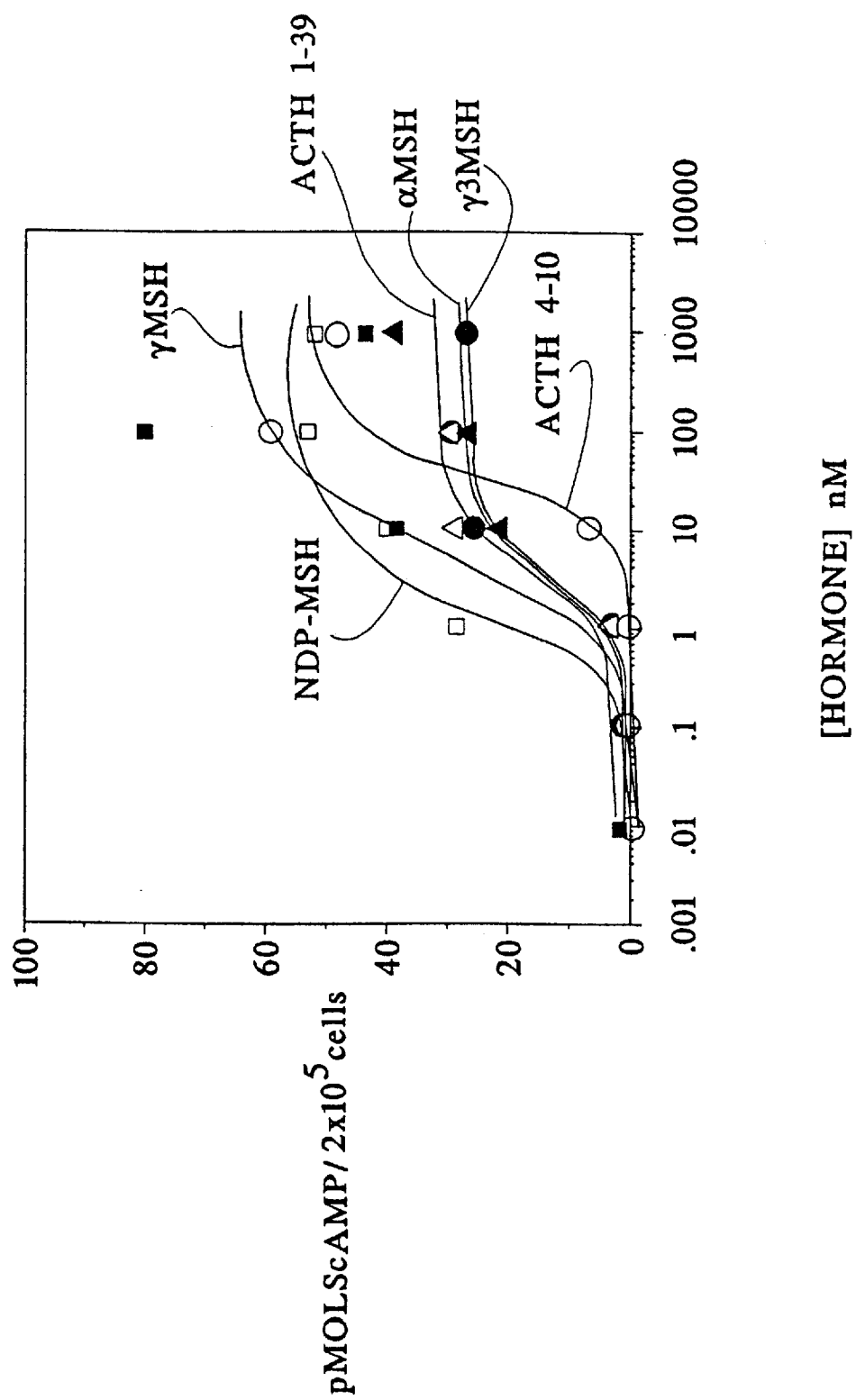
FIG. 3 illustrates cAMP production in recombinant MC3-R expressing human 293 cells upon binding of a variety of melanocortin receptor ligands at the indicated concentrations binding of melanocortin peptides to melanocortin-3 receptor.

The present invention relates to the cloning, expression and functional characterization of mammalian melanocortin receptor genes. The invention comprises a nucleic acid having a nucleotide sequence of a novel melanocortin receptor gene, termed MC3-R, that is responsive to γ-melanocyte stimulating hormone (γ-MSH). The invention provides a nucleic acid comprising a cDNA copy of a mRNA transcribed from the rat MC3-R gene and the deduced amino acid sequence of the cognate protein. Also provided by the invention is the tissue distribution pattern of expression of this gene.

This invention provides a nucleic acid comprising a cDNA copy of a rat mRNA of the MC3-R gene, a nucleic acid hybridization probe comprising DNA sequences of this rat cDNA, a recombinant eukaryotic expression construct capable of expressing the rat MC3-R protein in cultures of transformed eukaryotic cells and such cultures of transformed eukaryotic cells that synthesize the rat MC3-R protein, a homogeneous composition of the rat MC3-R protein, and antibodies against and epitopes of the rat MC3-R protein. Methods for the characterization of this receptor protein and the development of agents having pharmacological uses related to this receptor protein are also provided by the invention.

The present invention encompasses a nucleic acid having a nucleotide sequence encoding a rat melanocortin receptor that is the MC3-R receptor and that is derived from a cDNA molecule isolated from a rat cDNA library (SEQ ID No:3). In this embodiment of the invention, the nucleotide sequence includes 1339 nucleotides of the rat MC3-R gene comprising 972 nucleotides of coding sequence, 297 nucleotides of 5' untranslated sequence and 69 nucleotides of 3' untranslated sequence.

The invention provides a nucleic acid encoding a mammalian MC3-R, most preferably a rat MC3-R consisting essentially of the sequence depicted in FIGS. 1A–1C (SEQ ID No:3). The use of the term "consisting essentially of" herein is meant to encompass the disclosed sequence and includes allelic variations of this nucleotide sequence, either naturally occurring or the product of in vitro chemical or genetic modification. Each such variant will be understood to have essentially the same nucleotide sequence as the nucleotide sequence of the corresponding MC3-R disclosed herein. Similarly, the corresponding MC3-R protein molecule, having the deduced amino acid sequence consisting essentially of the sequence shown in FIGS. 2A–2C (SEQ ID No.:4), is also claimed as an aspect of the invention. MC3-R protein molecules provided by the invention are understood to have substantially the same biological properties as the MC3-R protein molecule encoded by the nucleotide sequence described herein.

In another aspect, the invention comprises a homogeneous composition of a 35.7 kilodalton mammalian MC3-R or derivative of, said size being understood to be the size of the protein before any post-translational modifications thereof. The amino acid sequence of the MC3-R or derivative thereof preferably consists essentially of the amino acid sequence of the rat MC3-R protein shown in FIGS. 2A–2C (SEQ ID No:4).

This invention provides both nucleotide and amino acid probes derived from the sequences herein provided. The invention includes probes isolated from either cDNA or genomic DNA, as well as probes made synthetically with the sequence information derived therefrom. The invention specifically includes but is not limited to oligonucleotide, nick-translated, random primed, or in vitro amplified probes made using cDNA or genomic clone embodying the invention, and oligonucleotide and other synthetic probes synthesized chemically using the nucleotide sequence information of cDNA or genomic clone embodiments of the invention.

It is a further object of this invention to provide sequences of a mammalian MC3-R gene, preferably the rat MC3-R gene, for use as nucleic acid hybridization probes to determine the pattern, amount and extent of expression of this receptor in various tissues of mammals, including humans. It is also an object of the present invention to provide nucleic acid hybridization probes derived from the sequences of the rat MC3-R gene to be used for the detection and diagnosis of genetic diseases. It is an object of this invention to provide nucleic acid hybridization probes derived from the DNA sequences of the rat MC3-R to be used for the detection of novel related receptor genes.

The present invention also includes synthetic peptides made using the nucleotide sequence information comprising the cDNA embodiment of the invention. The invention includes either naturally occurring or synthetic peptides which may be used as antigens for the production of MC3-R-specific antibodies, or used for competitors of the MC3-R molecule for drug binding, or to be used for the production of inhibitors of the binding of agonists or antagonists or analogues thereof to MC3-R molecules.

The present invention also provides antibodies against and epitopes of mammalian MC3-R receptors, preferably the rat MC3-R protein. It is an object of the present invention to provide antibodies that are immunologically reactive to mammalian MC3-R proteins. It is a particular object of the invention to provide monoclonal antibodies to mammalian MC3-R protein, most preferably rat or human MC3-R protein.

It is also an object of the present invention to provide a hybridoma cell line that produces such antibodies. It is a particular object of the invention to provide a hybridoma cell line that is the result of fusion between a non-immunoglobulin producing mouse myeloma cell line and spleen cells derived from a mouse immunized with a cell line which expresses an MC3-R antigen. The present invention also provides a hybridoma cell line that produces such an antibody, and that can be injected into a living mouse to provide an ascites fluid from the mouse that is comprised of such an antibody.

The present invention also provides a pharmaceutical composition comprising a therapeutically effective amount of a monoclonal antibody that is immunologically reactive to a mammalian MC3-R, preferably a rat or human MC3-R, and in a pharmaceutically acceptable carrier.

It is a further object of the present invention to provide an epitope of a mammalian MC3-R protein wherein the epitope is immunologically reactive to an antibody specific for mammalian MC3-R. In preferred embodiments, the epitope is derived from rat or human MC3-R protein.

It is another object of the invention to provide a chimeric antibody that is immunologically reactive to a mammalian MC3-R protein. In a preferred embodiment, the chimeric antibody is a monoclonal antibody. In a preferred embodiment, the MC3-R is a rat or human MC3-R.

The present invention provides a recombinant expression construct comprising the a nucleic acid having a nucleotide sequence of a mammalian MC3-R, preferably the rat MC3-R and sequences sufficient to direct the synthesis of rat MC3-R protein in cultures of transformed eukaryotic cells. In a preferred embodiment, the recombinant expression construct is comprised of plasmid sequences derived from the plasmid pcDNA/NEO I and cDNA of the rat MC3-R gene. This invention includes a recombinant expression construct comprising a nucleic acid consisting essentially of the nucleotide sequences encoding the rat MC3-R in an embodiment that provides for their expression in cultures of transformed eukaryotic cells.

It is also an object of this invention to provide cultures of transformed eukaryotic cells that have been transformed with such a recombinant expression construct and that synthesize mammalian, preferably rat or human, MC3-R protein. In a preferred embodiment, the invention provides human 293 cells that synthesize rat MC3-R protein.

The present invention also includes protein preparations of mammalian, preferably rat MC3-R, and preparations of membranes containing mammalian MC3-R, derived from cultures of transformed eukaryotic cells. In a preferred embodiment, cell membranes containing rat MC3-R protein are isolated from 293 cell cultures transformed with a recombinant expression construct that directs the synthesis of rat MC3-R protein.

It also an object of this invention to provide mammalian, preferably rat or human MC3-R for use in the in vitro screening of novel MSH agonist and antagonist compounds. In a preferred embodiment, membrane preparations containing the rat MC3-R, derived from cultures of transformed eukaryotic cells, are used to determine the drug dissociation properties of various novel MSH agonist and antagonist compounds in vitro. These properties are then used to characterize such novel compounds by comparison to the binding properties of known MC3-R agonists and antagonists.

The present invention is also useful for the in vivo detection of analogues of MSH agonists or antagonists, known or unknown, either naturally occurring or as the embodiments of a drug.

It is an object of the present invention to provide a method for the quantitative detection of agonists or antagonists, or analogues thereof, of the MC3-R protein, known or unknown, either naturally occurring or as the embodiments of a drug. It is an additional object of the invention to provide a method to detect such agonists, antagonists, or analogues thereof in blood, saliva, semen, cerebrospinal fluid, plasma, lymph, or any other bodily fluid.

Specific preferred embodiments of the present invention will become evident from the following more detailed description of certain preferred embodiments and the claims.

DETAILED DESCRIPTION OF THE PREFERRED EMBODIMENTS

The term "melanocortin-3 receptor" (MC3-R) as used herein refers to proteins consisting essentially of, and having substantially the same biological activity as, the protein encoded by the nucleic acid depicted in FIG. 1 (SEQ ID No:3). This definition is intended to encompass natural allelic variations in the MC3-R sequence. Cloned nucleic acid provided by the present invention may encode MC3-R protein of any species of origin, including, for example, mouse, rat, rabbit, cat, and human, but preferably the nucleic acid provided by the invention encodes MC3-R receptors of mammalian, most preferably rat and human, origin.

Nucleic acid hybridization probes provided by the invention are DNAs consisting essentially of the nucleotide sequence depicted in FIG. 1 (SEQ ID No:3), or any portion thereof effective in nucleic acid hybridization. Nucleic acid probes are useful for detecting MC3-R gene expression in cells and tissues using techniques well-known in the art, including but not limited to Northern blot hybridization, in situ hybridization and Southern hybridization to reverse transcriptase - polymerase chain reaction product DNAs. The probes provided by the present invention, including oligonucleotides probes derived therefrom, are useful are also useful for Southern hybridization of mammalian, preferably human, genomic DNA for screening for restriction fragment length polymorphism (RFLP) associated with certain genetic disorders.

The production of proteins such as the MC3-R from cloned genes by genetic engineering means is well known in this art. The discussion which follows is accordingly intended as an overview of this field, and is not intended to reflect the full state of the art.

DNA which encodes the MC3-R may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the MC3-R gene sequence information provided herein. Probes may be labeled with a detectable group such as a fluorescent group, a radioactive atom or a chemiluminescent group in accordance with known procedures and used in conventional hybridization assays, as described in greater detail in the Examples below. In the alternative, MC3-R gene sequences may be obtained by use of the polymerase chain reaction (PCR) procedure, with the PCR oligonucleotide primers being produced from the MC3-R gene sequence provided herein. See U.S. Pat. Nos. 4,683,195 to Mullis et al. and 4,683,202 to Mullis.

MC3-R protein may be synthesized in host cells transformed with a recombinant expression construct comprising a nucleic acid encoding the MC3-R. Such a recombinant expression construct can also be comprised of a vector that is a replicable DNA construct. Vectors are used herein either to amplify DNA encoding the MC3-R and/or to express DNA which encodes MC3-R. For the purposes of this invention, a recombinant expression construct is a replicable DNA construct in which a DNA sequence encoding the MC3-R is operably linked to suitable control sequences capable of effecting the expression of the MC3-R in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1990, *Molecular Cloning: A Laboratory Manual* (Cold Spring Harbor Press: New York).

Vectors useful for practicing the present invention include plasmids, viruses (including phage), retroviruses, and integrable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is the plasmid pcDNA/NEO I. Transformed host cells are cells which have been transformed or transfected with recombinant expression constructs made using recombinant DNA techniques and comprising mammalian MC3-R-encoding sequences. Preferred host cells are human 293 cells. Transformed host cells may ordinarily express MC3-R protein, but host cells transformed for purposes of cloning or amplifying nucleic acid hybridization probe DNA need not express the receptor. When expressed, the mammalian MC3-R protein will typically be located in the host cell membrane. See, Sambrook et al., ibid.

Cultures of cells derived from multicellular organisms are a desirable host for recombinant MC3-R protein synthesis. In principal, any higher eukaryotic cell culture is workable, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human 293 cells, VERO and HeLa cells, Chinese hamster ovary (CHO) cell lines, and WI138, BHK, COS-7, CV, and MDCK cell lines. Human 293 cells are preferred.

The invention provides homogeneous compositions of mammalian MC3-R protein produced by transformed eukaryotic cells as provided herein. Such homogeneous compositions are intended to be comprised of mammalian MC3-R protein that comprises at least 90% of the protein in such homogenous composition. The invention also provides membrane preparation from cells expressing MC3-R as the result of transformation with a recombinant expression construct, as described here.

Mammalian MC3-R protein made from cloned genes in accordance with the present invention may be used for screening agonist compounds for MC3-R activity, or for determining the amount of a MC3-R agonist or antagonist drug in a solution (e.g., blood plasma or serum). For example, host cells may be transformed with a recombinant expression construct of the present invention, MC3-R protein expressed in those host cells, the cells lysed, and the membranes from those cells used to screen compounds for MC3-R binding activity. Competitive binding assays in which such procedures may be carried out are well known in the art. By selection of host cells which do not ordinary express MC3-Rs, pure preparations of membranes containing MC3-Rs can be obtained. Further, MC3-R agonists and antagonists can be identified by transforming host cells with a recombinant expression construct as provided by the present invention. Membranes obtained from such cells can be used in binding studies wherein the drug dissociation activity is monitored.

The recombinant expression constructs of the present invention are useful in molecular biology to transform cells which do not ordinarily express the MC3-R to thereafter express this receptor. Such cells are useful as intermediates for making cell membrane preparations useful for receptor binding assays, which are in turn useful for drug screening. The recombinant expression constructs of the present invention are also useful in gene therapy. Cloned genes of the present invention, or fragments thereof, may also be used in gene therapy carried out homologous recombination or site-directed mutagenesis. See generally Thomas & Capecchi, 1987, Cell 51: 503–512; Bertling, 1987, Bioscience Reports 7: 107–112; Smithies et al., 1985, Nature 317: 230–234.

Oligonucleotides of the present invention are useful as diagnostic tools for probing MC3-R gene expression in tissues. For example, tissues are probed in situ with oligonucleotide probes carrying detectable groups by conventional autoradiographic techniques, as explained in greater detail in the Examples below, to investigate native expression of this receptor or pathological conditions relating thereto. Further, chromosomes can be probed to investigate the presence or absence of the MC3-R gene, and potential pathological conditions related thereto, as also illustrated by the Examples below.

The invention also provides antibodies that are immunologically reactive to a mammalian MC3-R, preferably rat or human MC3-R. The antibodies provided by the invention are raised in animals by inoculation with cells that express a mammalian MC3-R or epitopes thereof, using methods well known in the art. Animals that are used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses a mammalian MC3-R, or any cell or cell line that expresses a mammalian MC3-R or any epitope thereof as a result of molecular or genetic engineering, or that has been treated to increase the expression of a mammalian MC3-R by physical, biochemical or genetic means. Preferred cells are human cells, most preferably human 293 cells that have been transformed with a recombinant expression construct comprising a nucleic acid encoding a mammalian MC3-R, preferably a rat or human MC3-R, and that express the mammalian MC3-R gene product.

The present invention provides monoclonal antibodies that are immunologically reactive with an epitope that is a mammalian MC3-R or fragment thereof and that is present on the surface of mammalian cells, preferably human or mouse cells. These antibodies are made using methods and techniques well known to those of skill in the art.

Monoclonal antibodies provided by the present invention are produced by hybridoma cell lines, that are also provided by the invention and that are made by methods well known in the art. Hybridoma cell lines are made by fusing individual cells of a myeloma cell line with spleen cells derived from animals immunized with cells expressing a mammalian MC3-R, preferably rat or human cells, as described above. The myeloma cell lines used in the invention include lines derived from myelomas of mice, rat, hamsters, primates and humans. Preferred myeloma cell lines are from mouse, and the most preferred mouse myeloma cell line is P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of a mammalian MC3-R.

The present invention encompasses fragments of the antibody that are immunologically reactive with an epitope of a mammalian MC3-R. Such fragments are produced by any number of methods, including but not limited to proteolytic cleavage, chemical synthesis or preparation of such fragments by means of genetic engineering technology. The present invention also encompasses single-chain antibodies that are immunologically reactive with an epitope of a mammalian MC3-R made by methods known to those of skill in the art.

The present invention also encompasses an epitope of a mammalian MC3-R that is comprised of sequences and/or a conformation of sequences present in the mammalian MC3-R molecule. This epitope may be naturally occurring, or may be the result of proteolytic cleavage of the mammalian MC3-R molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to an epitope that is a mammalian MC3-R. The chimeric antibodies embodied in the present invention include those that are derived from naturally occurring antibodies as well as chimeric antibodies made by means of genetic engineering technology well known to those of skill in the art.

The Examples which follow are illustrative of specific embodiments of the invention, and various uses thereof. They set forth for explanatory purposes only, and are not to be taken as limiting the invention.

EXAMPLE 1

Isolation of an αMSH Receptor Probe by Random PCR Amplification of Human Melanoma cDNA Using Degenerate Oligonucleotide Primers In order to clone novel G-protein coupled receptors, cDNA prepared from RNA from human melanoma cells was used as template for a polymerase chain reaction (PCR)-based random cloning experiment. PCR was performed using a pair of degenerate oligonucleotide primers corresponding to the putative third and sixth transmembrane regions of G-protein coupled receptors (Libert et al., 1989, Science 244: 569–72; Zhou et al., 1990, Nature 347: 76–80). The PCR products obtained in this experiment were characterized by nucleotide sequencing. Two novel sequences representing novel G-protein-coupled receptors were identified.

PCR amplification was performed as follows. Total RNA was isolated from a human melanoma tumor sample by the guanidinium thiocyanate method (Chirgwin et al., 1979, Biochemistry 18: 5294–5299). Double-stranded cDNA was synthesized from total RNA with murine reverse transcriptase (BRL, Gaithersburg, Md.) by oligo-dT priming (Sambrook et al., ibid.). The melanoma cDNA mixture was then subjected to 45 cycles of PCR amplification using 500 picomoles of degenerate oligonucleotide primers having the following sequence: Primer III (sense):

GAGTCGACCTGTG(C/T)G(C/T)(C/G)AT(C/T)(A/G)CIIT(G/T)GAC(C/A)G(C/G)TAC (SEQ ID NO: 1)

and

Primer VI (antisense):

CAGAATTCAG(T/A)AGGGCAICCAGCAGAI(G/C)(G/A)(T/C)GAA (SEQ ID NO:2)

in 100 μl of a solution containing 50 mM Tris-HCl (pH 8.3), 2.5 mM MgCl$_2$, 0.01% gelatin, 200 μM each dNTP, and 2.5 units of Taq polymerase (Saiki et al., 1988, Science 239: 487–491). These primers were commercially synthesized by Research Genetics Inc. (Huntsville, Ala.). Each PCR amplification cycle consisted of incubations at 94° C. for 1 min (denaturation), 45° C. for 2 min (annealing), and 72° C. for 2 min (extension).

Amplified products of the PCR reaction were extracted with phenol/chloroform and precipitated with ethanol. After digestion with EcoRI and SalI, the PCR products were separated on a 1.2% agarose gel. A slice of this gel, corresponding to PCR products of 300 basepairs (bp) in size, was cut out and purified using glass beads and sodium iodide, and the insert was then cloned into a pBKS cloning vector (Stratagene, LaJolla, Calif.).

A total of 172 of such pBKS clones containing inserts were sequenced using Sequenase (U.S. Biochemical Corp., Cleveland, Ohio) by the dideoxynucleotide chain termination method (Sanger et al., 1977, Proc. Natl. Acad. Sci. USA 74: 5463–5467). Two types of sequences homologous to other G-protein coupled receptors were identified by sequence comparison of the isolated clones.

EXAMPLE 2

Isolation of an Mouse αMSH Receptor cDNA

Probes isolated in Example 1 was used to screen a Cloudman melanoma cDNA library in order to isolate a full-length cDNA corresponding to the cloned probe. One clone was isolated from a library of 5×10$^6$ clones screened as described below. This clone contained an insert of 2.6 kilobases (kb). The nucleotide sequence of the complete coding region was determined (see co-pending U.S. patent application Ser. No. 07/866,979, incorporated by reference).

EXAMPLE 3

Isolation of a Rat γ-MSH Receptor cDNA

The mouse αMSH receptor cDNA isolated as described in Example 2 and co-pending U.S. patent application Ser. No. 07/866,979 was used to screen a rat hypothalamus cDNA library at low stringency (30% formamide, 5×SSC, 0.1% sodium pyrophosphate, 0.2% sodium dodecyl sulfate, 100 μg/ml salmon sperm DNA, and 10% Denhardt's solution) at 42° C. for 18 h. A 1 kb cDNA clone was isolated and sequenced as described in co-pending U.S. patent application Ser. No. 07/866,979, and this clone used to re-screen the rat hypothalamus cDNA library at high stringency (same conditions as above except that formamide was present at 45%). A cDNA clone approximately 2.0 kb in length was isolated; a portion of this cDNA comprising the coding region was sequenced and is shown in FIGS. 1A–1C (SEQ ID No:3). The putative protein product of the gene is also shown in FIGS. 1A–1C (SEQ ID No:4). The coding sequence comprises 972 nucleotides encoding a protein 323 amino acids in length, and having a predicted molecular weight of 35.7 kilodaltons prior to post-translational modification. This cloned nucleic acid was found to be a novel γ-MSH receptor and termed the melanocortin-3 receptor (MC3-R).

The predicted amino acid sequences of this novel receptor (MC3-R), mouse αMSH$^R$, human MSH$^R$, human ACTH$^R$ and bovine ACTH$^R$ are aligned in FIGS. 2A–2C. Bars indicate predicted transmembrane regions I through VII in the protein product of the gene. The novel melanocortin-3 receptor described herein shares 43% sequence homology with the previously described αMSH receptor isolated from the mouse (see co-pending U.S. patent application Ser. No. 07/866,979). This sequence comparison defines the melanocortin receptors as a novel subfamily of the G protein-coupled receptors with a number of unusual features. The melanocortin receptors are the smallest G protein-coupled receptors identified to date (297–323 amino acids) resulting form a short amino terminal extracellular domain, a short carboxy-terminal intracellular domain, and a very small third intracellular loop. The melanocortin receptors lack several amino acid residues present in most G protein coupled receptors (see Probst et al., 1992, DNA & Cell Biol. 11: 1–20), including the proline residues in the 4th and 5th transmembrane domains, and one or both of the cysteine residues thought to form a disulfide bond between the first and second extracellular loops (see Dixon et al., 1987, EMBO J. 6: 3269–3275 and Karnik et al., 1988, Proc. Natl. Acad. Sci. USA 85: 8459–8463). Remarkably, the melanocortin receptors do not appear highly related to the other G protein-coupled receptors which recognize peptide ligands, such as the receptors for bombesin (see Spindel et al., 1990, Mol. Endocrinol. 4: 1956–1963) or substance K (see Masu et al., 1987, Nature 329: 836–838) but rather, are more closely related to the receptor for $\Delta^9$-tetahydrocannabinol (see Matsuda et al., 1990, Nature 346: 561–564). The cannabinoid receptor also lacks the conserved proline in transmembrane V and the cysteine in the first extracellular loop necessary for disulfide bond formation. Least parsimony analysis of these receptors suggests that they may be evolutionarily related and form a subfamily district from the peptide receptors and the amine receptors.

The MC3-R receptor is the first neural melanocortin receptor isolated from neural tissues, as well as being the first γ-MSH receptor isolated. Thus, the embodiments of this receptor comprising the instant invention are useful in determining the role of melanocortins in the brain, particularly the function of γ-MSH, in the identification of other neural melanocortin receptors, and in the development of neural melanocortin receptor-specific agonists and antagonists having useful pharmacological properties.

EXAMPLE 4

Construction of a Rat MC3-R Recombinant Expression Construct, DNA Transfection and Functional Expression of the MC3-R Gene Product In order to biochemically characterize the rat MC3-R cDNA isolated as in Example 3, and to confirm that it encodes a melanocortin receptor, this cDNA was cloned into a mammalian expression construct, the resulting recombinant expression construct transfected into human 293 cells, and cell lines generated that expressed the MC3-R protein in cellular membranes at the cell surface. Such cells and membranes isolated from such cells were used for biochemical characterization experiments described below.

The entire coding region of the MC3-R cDNA insert, contained in a 2.0 kb restriction enzyme digestion fragment, was cloned into the BamHI/XhoI sites of pcDNA/NEO I expression vector (Invitrogen, San Diego, Calif.). The resulting plasmid was prepared in large-scale through one cycle of CsCl gradient ultracentrifugation and 20 µg pcDNA-MC3-R DNA were transfected into each 100 mm dish of 293 cells using the calcium phosphate method (see Chen & Okayama, 1987, Mol. Cell. Biol. 7: 2745–2752). After transfection, cells were cultured in DMEM media supplemented with 10% calf serum in a 3% $CO_2$ atmosphere at 37° C. Selection was performed with neomycin (G418; GIBCO) at a concentration of 1000 µg/ml; selection was started 72 h after transfection and continued for 3 weeks.

Specific binding of melanocortin peptides to cells expressing the MC3-R receptor was demonstrated by competition experiments using $^{125}$I-labeled Nle$^4$-D-Phe$^7$-α-MSH (NDP-MSH, as described in Tatro et al., 1990, Cancer Res. 50: 1237–1242). Suspended cells ($2\times10^5$) were incubated at 37° C. with 500,000 cpm of labeled peptide for 10 min in binding buffer (Ham's F10 media plus 10 mM HEPES, pH 7.2, 0.25% bovine serum albumin, 500 K IU/ml aprotinin, 100 µg/ml bacitracin and 1 mM 1,10-phenanthroline) in the presence or absence of the indicated concentrations of peptides. Maximum labelling was achieved within 10 min.

Labeled NDP-MSH binding to cells expressing MC3-R, produced as described above, is inhibited by competition with unlabeled peptides known to be melanocortin receptor agonists, having a relative order of potency as follows:

NDP-MSH>γ-MSH>α-MSH>ACTH$_{4-10}$>>>ORG2766. Approximate $K_i$ values derived from this experiment are as shown in Table I:

TABLE I

| Agonist | $K_i$ (approx) |
| --- | --- |
| NDP-MSH | $2 \times 10^{-8}$ |
| γ-MSH | $5 \times 10^{-8}$ |
| α-MSH | $1 \times 10^{-7}$ |
| ACTH$_{4-10}$ | $8 \times 10^{-5}$ |

Melanocortin receptors are known to couple to G-proteins and thereby activate adenylate cyclase, increasing intracellular levels of cAMP (see Buckley & Ramachandran, 1981, Proc. Natl. Acad. Sci. USA 78: 7431–7435; Grahame-Smith et al., 1967, J. Biol. Chem. 242: 5535–5541; Mertz & Catt, 1991, Proc. Natl. Acad. Sci. USA 88: 8525–8529; Pawalek et al., 1976, Invest. Dermatol. 66: 200–209). This property of cells expressing melanocortin receptors was used to analyze expression of MC3-R in cells transfected with the expression vectors described herein as follows.

Cells (~$5\times10^6$) were plated in 6-well dishes, washed once with DMEM containing 1% bovine serum albumin (BSA) and 0.5 mM IBMX (a phosphodiesterase inhibitor), then incubated for 1 h at 37° C. with varying concentrations of the melanotropic peptides αMSH, γ$_3$MSH, γMSH, the MSH peptide analogues Nle$^4$-D-Phe$^7$-αMSH (NDP-MSH), ACTH$_{4-10}$ and ACTH$_{1-39}$. Following hormone treatment, the cells were washed twice with phosphate buffered saline and intracellular cAMP extracted by lysing the cells with 1 ml of 60% ethanol. Intracellular cAMP concentrations were determined using an assay which measures the ability of cAMP to displace [8-$^3$H] cAMP from a high affinity cAMP binding protein (see Gilman, 1979, Proc. Natl. Acad. Sci. USA 67: 305–312).

The results of these experiments are shown in FIG. 3. The abscissa indicates the concentration of each hormone and the ordinate indicates the percentage of basal intracellular cAMP concentration achieved by each treatment. Points indicate the mean of duplicate incubations; the standard error did not exceed 15% for any data point. None of the peptides tested induced any change in intracellular cAMP in cells containing the vector alone. Cells expressing rat MC3-R responded strongly to every melanotropic peptide containing the MSH code sequence His-Phe-Arg-Trp, with up to a 60-fold elevation of intracellular cAMP levels. EC$_{50}$ values ranged from 1–50 nM. The most potent ligand and the one having the lowest EC$_{50}$ was found to be γMSH. The order of potency for the naturally occurring melanocortins was found to be:

$\alpha_2\text{-MSH}=\gamma\text{MSH}>\alpha\text{MSH}=\text{ACTH}_{1-39}>\gamma_3\text{-MSH}>\text{des-acetyl-}\alpha\text{MSH}>\text{ACTH}_{4-10}$.

Ec$_{50}$ values for these compounds are shown in Table II:

TABLE II

| Agonist | Ec$_{50}$ |
| --- | --- |
| NDP-MSH | $1 \times 10^{-9}$ |
| $\gamma_1$-MSH | $3 \times 10^{-9}$ |
| $\gamma_2$-MSH | $3 \times 10^{-9}$ |
| $\alpha$-MSH | $4 \times 10^{-9}$ |
| ACTH$_{1-39}$ | $4 \times 10^{-9}$ |
| $\gamma_3$-MSH | $6 \times 10^{-9}$ |
| desacetyl-$\alpha$MSH | $8 \times 10^{-9}$ |
| ACTH$_{4-10}$ | $1 \times 10^{-7}$ |

Additionally, a synthetic melanocortin peptide (ORG2766), known to have the greatest activity in vivo in stimulation of retention of learned behavior and in stimulation of neural regeneration, was unable to stimulate MC3-R-mediated cAMP production, and was also inactive as an antagonist. The results strongly indicate that this peptide does not bind to MC3-R protein.

The results of these analyses indicate that the nucleic acid isolated and described herein is the first known receptor responsive to γMSH.

EXAMPLE 5

Tissue Distribution of MC3-R Expression

Figure 4:
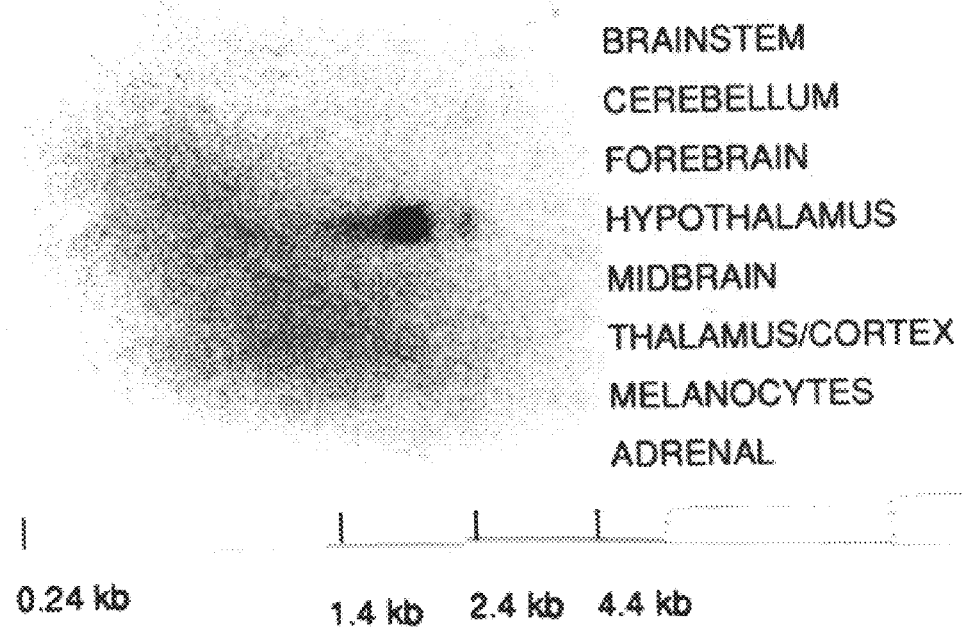
FIG. 4 illustrates expression of MC3-R mRNA in a variety of rat tissues by Northern blot hybridization.

To further gain insight into rat MC3-R, the tissue distribution of mRNA corresponding to expression of this receptor gene from various tissues was determined by Northern hybridization experiments (see Sambrook et al., ibid.). The results of these experiments are shown in FIG. 4.

A panel of tissue samples was examined by Northern hybridization analysis performed under high stringency conditions. A nitrocellulose filter was hybridized successively with rat MC3-R probe to determine the distribution of receptor mRNA. These results are depicted in FIG. 4. Each lane contains 4 pg of poly A$^+$ RNA from the brain region or tissue indicated. Melanocyte RNA was isolated from Cloudman S91 melanoma cell line. Briefly, total RNA was prepared using the guanidinium thiocyanate procedure (see Sambrook et al., Ibid.) followed by poly A$^+$ purification using the Poly A Track mRNA isolation system (Promega Biotech, Madison, Wis.). Poly A$^+$ RNAs were analyzed by electrophoresis on a 2.2M formaldehyde/1.2% agarose gel, transferred by capillary blotting to a nylon membrane (MSI) and hybridized with 1 kb EcoRI fragment of the MC3-R cDNA under stringent conditions (50% formamide, 5×SSC, 0.1% sodium pyrophosphate, 0.3% sodium dodecyl sulfate, 100 pg/ml salmon sperm DNA and 10% Denhardt's solution) at 42° C. for 18 h. Northern blots were visualized by autoradiography.

In hypothalamus, the rat MC3-R is expressed as two mRNA species of 2.5 and 2.0 kb. No MC3-R mRNA was detected in melanocytes or adrenal gland, in contrast to previously-described receptors for ACTH and αMSH (see co-pending U.S. patent application Ser. Nos. 07/866,979 and 07/866,560, herein incorporated by reference). Also, no MC3-R mRNA was detected in heart, liver, lung, testes, thyroid or in any other brain region besides the hypothalamus, even when an excess (20 μg) of RNA was analyzed.

Additionally, in situ hybridization of rat brain section was performed using a MC3-R probe. Briefly, these experiments were performed as follows. Male Sprague-Dawley rats (200 g) were anesthetized and perfused at 40° C. with 1 L of 4% paraformaldehyde in borate buffer, pH 9.5 (fixation buffer). Brains were dissected and incubated in fixation buffer for 8 h, then further incubated overnight in fixation buffer containing 10% sucrose. Brains were then sectioned serially into 10 series of 30 μm slices with a sliding microtome. Sections were prepared and hybridized as described in Arriza et al., 1988, Neuron 1: 887–900. A 400 bp fragment of the MC3-R cDNA was subcloned into a pBKS vector (Stratagene) and used to synthesize an antisense cRNA probe (see Sambrook et al., ibid.) Sections were hybridized at 65° C. for 24 h with $^{35}$S-labeled probe (~1×10$^7$ cpm/ml) in 65% formamide, 0.26M NaCl, 1.3×Denhardt's solution, 13 mM Tris (pH 8.0), 1.3 mM EDTA and 13% dextran sulfate. Slides were washed in 4×SSC (0.6M NaCl, 0.06M Na citrate), digested with RNase (20 pg/ml) for 30 min at 37° C.), and then rinsed to a final stringency of 0.1×SSC at 65° C. for 30 min. Sections were dehydrated, dipped in NTB-2 emulsion, and developed after 21 days.

Figure 5:
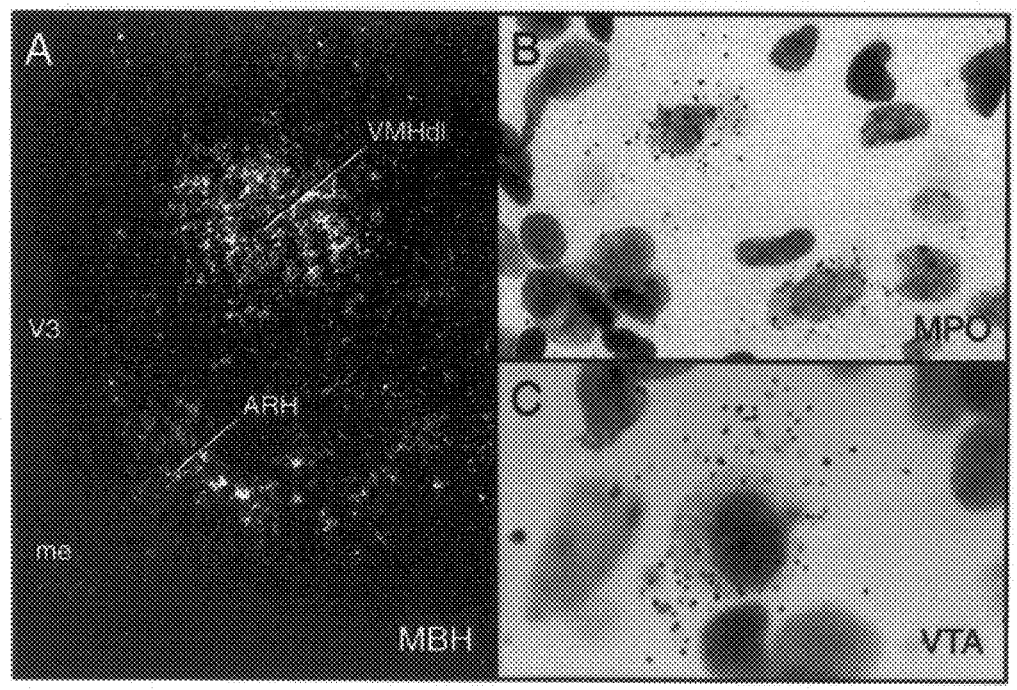
FIG. 5 illustrates expression of MC3-R mRNA in certain regions of rat brain by in situ hybridization.

Results of these experiments are shown in FIG. 5. These experiments localized MC3-R expression to different regions of the hypothalamus and limbic system. Panel A of FIG. 5 shows darkfield microscopy (X25) of the medial basal portion of the tuberal hypothalamus (MBH) and third ventricle (V3), showing MC3-R positive cells in the arcuate nucleus of the hypothalamus (ARH), dorsomedial portion of the ventromedial nucleus of the hypothalamus (VMHd1), and median eminence (me). Panels B and C of FIG. 5 show brightfield microscopy (X800 and X1500, respectively) of representative MC3-R positive neurons in the medial preoptic area (MPO) of the hypothalamus and the ventral tegmental area (VTA). The complete distribution of MC3-R mRNA detected is: hypothalamus (AVP, AVPv, MPNm, perifx, PVpo, AHNa, LHA, ARH, VMHd1, PH, PVp, PMv, PMd, SUM); septum (LSi, BSTdm, a1); hippocampus (CAI-3); olfactory cortex (PRI); thalamus (CMc, RhT, PVT, MH); amygdala (AAA); and other (PAG, VTA, IF interfascicular nuclei, CL central linear nuclei of raphe). Abbreviations used herein are from Simerly et al., 1992 J. Comp. Neur. 294: 76–95.

These results are in contrast to analyses of brain tissue for ACTH$^R$ or MSH$^R$ expression, in which none was detected, despite extensive documentation of MSH binding sites in the brain as well as in other tissues (see co-pending U.S. patent application Ser. No. 07/866,979). The findings disclosed herein demonstrate the existence of alternate forms of receptors related to MSH$^R$ that are specifically expressed in brain tissue.

It should be understood that the foregoing disclosure emphasizes certain specific embodiments of the invention and that all modifications or alternatives equivalent thereto are within the spirit and scope of the invention as set forth in the appended claims.

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..35
        (D) OTHER INFORMATION: /function= "Degenerate
            oligonucleotide primer (sense)"
            /note= "The residues at positions 23 and 24 are
            inosine"

(xi) SEQUENCE DESCRIPTION: SEQ ID NO: 1:

GAGTCGACCT GTGYGYSATY RCNNTKGACM GSTAC                                    35

(2) INFORMATION FOR SEQ ID NO: 2:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 1..32
        (D) OTHER INFORMATION: /function= "Degenerate
            oligonucleotide primer (antisense)"
            /note= "The nucleotide at position 18 is inosine"

(xi) SEQUENCE DESCRIPTION: SEQ ID NO: 2:

CAGAATTCAG WAGGGCANCC AGCAGASRYG AA                                       32

(2) INFORMATION FOR SEQ ID NO: 3:

(i) SEQUENCE CHARACTERISTICS:
        (A) LENGTH: 1338 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: 5'UTR
        (B) LOCATION: 1..297

(ix) FEATURE:
        (A) NAME/KEY: CDS
        (B) LOCATION: 298..1269

(ix) FEATURE:
        (A) NAME/KEY: 3'UTR
        (B) LOCATION: 1270..1338

(xi) SEQUENCE DESCRIPTION: SEQ ID NO: 3:

GGCTGTAACT GTAGCAACCG GTGTTGGGTG GGGATGAGAA GAGACCAGAG AGAGAGAGGG    60

-continued

```
TCAGAGCGAC AGGGGATGAG ACAGGCTGGT CAGAGTCTGC ACTGATTGTT GGAGACGCAA    120

AGGAAAGTTT TTTCTATGTC TCCAACCTCC CCCTCCTCCC CCGTTTCTCT CTGGAGAAAC    180

TAAAATCTAG ACTGGACAGC ATCCACAAGA GAAGCACCTA GAAGAAGATT TTTTTTTCCC    240

AGCAGCTTGC TCAGGACCCT GCAGGAGCTG CAGCCGGAAC TGGTCCCGCC GATAACC      297
```

| | | | | | | | | | | | | | | | | |
|---|---|---|---|---|---|---|---|---|---|---|---|---|---|---|---|---|
| ATG | AAC | TCT | TCC | TGC | TGC | CCG | TCC | TCC | TCT | TAT | CCG | ACG | CTG | CCT | AAC | 345 |
| Met | Asn | Ser | Ser | Cys | Cys | Pro | Ser | Ser | Ser | Tyr | Pro | Thr | Leu | Pro | Asn | |
| 1 | | | | 5 | | | | | 10 | | | | | 15 | | |
| CTC | TCC | CAG | CAC | CCT | GCA | GCC | CCC | TCT | GCC | AGC | AAC | CGG | AGT | GGC | AGT | 393 |
| Leu | Ser | Gln | His | Pro | Ala | Ala | Pro | Ser | Ala | Ser | Asn | Arg | Ser | Gly | Ser | |
| | | | 20 | | | | | 25 | | | | | 30 | | | |
| GGG | TTC | TGC | GAG | CAG | GTT | TTC | ATC | AAG | CCA | GAG | GTC | TTC | CTG | GCA | CTG | 441 |
| Gly | Phe | Cys | Glu | Gln | Val | Phe | Ile | Lys | Pro | Glu | Val | Phe | Leu | Ala | Leu | |
| | | 35 | | | | | 40 | | | | | 45 | | | | |
| GGC | ATC | GTC | AGT | CTG | ATG | GAA | AAC | ATC | CTG | GTG | ATC | CTG | GCT | GTG | GTG | 489 |
| Gly | Ile | Val | Ser | Leu | Met | Glu | Asn | Ile | Leu | Val | Ile | Leu | Ala | Val | Val | |
| | | 50 | | | | | 55 | | | | | 60 | | | | |
| AGG | AAC | GGC | AAC | CTG | CAC | TCC | CCC | ATG | TAC | TTC | TTC | CTG | CTG | AGC | CTG | 537 |
| Arg | Asn | Gly | Asn | Leu | His | Ser | Pro | Met | Tyr | Phe | Phe | Leu | Leu | Ser | Leu | |
| 65 | | | | | 70 | | | | | 75 | | | | | 80 | |
| CTG | CAG | GCC | GAC | ATG | CTG | GTG | AGC | CTG | TCC | AAC | TCC | CTG | GAG | ACC | ATC | 585 |
| Leu | Gln | Ala | Asp | Met | Leu | Val | Ser | Leu | Ser | Asn | Ser | Leu | Glu | Thr | Ile | |
| | | | | 85 | | | | | 90 | | | | | 95 | | |
| ATG | ATC | GTG | GTT | ATC | AAC | AGC | GAC | TCC | CTG | ACC | TTG | GAG | GAC | CAA | TTC | 633 |
| Met | Ile | Val | Val | Ile | Asn | Ser | Asp | Ser | Leu | Thr | Leu | Glu | Asp | Gln | Phe | |
| | | | 100 | | | | | 105 | | | | | 110 | | | |
| ATC | CAG | CAC | ATG | GAC | AAC | ATC | TTC | GAC | TCT | ATG | ATC | TGC | ATC | TCC | CTG | 681 |
| Ile | Gln | His | Met | Asp | Asn | Ile | Phe | Asp | Ser | Met | Ile | Cys | Ile | Ser | Leu | |
| | | 115 | | | | | 120 | | | | | 125 | | | | |
| GTG | GCC | TCC | ATC | TGC | AAC | CTC | CTG | GCC | ATC | GCC | GTG | GAC | AGG | TAC | GTC | 729 |
| Val | Ala | Ser | Ile | Cys | Asn | Leu | Leu | Ala | Ile | Ala | Val | Asp | Arg | Tyr | Val | |
| | | 130 | | | | | 135 | | | | | 140 | | | | |
| ACC | ATC | TTC | TAT | GCC | CTC | CGT | TAC | CAC | AGC | ATC | ATG | ACG | GTT | AGG | AAA | 777 |
| Thr | Ile | Phe | Tyr | Ala | Leu | Arg | Tyr | His | Ser | Ile | Met | Thr | Val | Arg | Lys | |
| 145 | | | | | 150 | | | | | 155 | | | | | 160 | |
| GCC | CTC | TCC | TTG | ATC | GTG | GCC | ATC | TGG | GTC | TGC | TGT | GGC | ATC | TGC | GGC | 825 |
| Ala | Leu | Ser | Leu | Ile | Val | Ala | Ile | Trp | Val | Cys | Cys | Gly | Ile | Cys | Gly | |
| | | | | 165 | | | | | 170 | | | | | 175 | | |
| GTG | ATG | TTC | ATC | GTC | TAC | TCC | GAG | AGC | AAG | ATG | GTC | ATC | GTG | TGC | CTC | 873 |
| Val | Met | Phe | Ile | Val | Tyr | Ser | Glu | Ser | Lys | Met | Val | Ile | Val | Cys | Leu | |
| | | | 180 | | | | | 185 | | | | | 190 | | | |
| ATC | ACC | ATG | TTC | TTC | GCC | ATG | GTG | CTC | CTC | ATG | GGC | ACC | CTG | TAC | ATC | 921 |
| Ile | Thr | Met | Phe | Phe | Ala | Met | Val | Leu | Leu | Met | Gly | Thr | Leu | Tyr | Ile | |
| | | 195 | | | | | 200 | | | | | 205 | | | | |
| CAC | ATG | TTC | CTC | TTC | GCC | AGG | CTG | CAC | GTC | CAG | CGC | ATC | GCG | GCA | CTG | 969 |
| His | Met | Phe | Leu | Phe | Ala | Arg | Leu | His | Val | Gln | Arg | Ile | Ala | Ala | Leu | |
| | | 210 | | | | | 215 | | | | | 220 | | | | |
| CCA | CCT | GCT | GAC | GGG | GTA | GCC | CCG | CAG | CAG | CAC | TCG | TGC | ATG | AAG | GGG | 1017 |
| Pro | Pro | Ala | Asp | Gly | Val | Ala | Pro | Gln | Gln | His | Ser | Cys | Met | Lys | Gly | |
| 225 | | | | | 230 | | | | | 235 | | | | | 240 | |
| GCC | GTC | ACC | ATC | ACC | ATC | CTG | CTG | GGG | GTT | TTC | ATC | TTC | TGC | TGG | GCG | 1065 |
| Ala | Val | Thr | Ile | Thr | Ile | Leu | Leu | Gly | Val | Phe | Ile | Phe | Cys | Trp | Ala | |
| | | | | 245 | | | | | 250 | | | | | 255 | | |
| CCT | TTC | TTC | CTC | CAC | CTG | GTC | CTC | ATC | ATC | ACC | TGC | CCC | ACC | AAC | CCC | 1113 |
| Pro | Phe | Phe | Leu | His | Leu | Val | Leu | Ile | Ile | Thr | Cys | Pro | Thr | Asn | Pro | |
| | | | | 260 | | | | | 265 | | | | | 270 | | |
| TAC | TGC | ATC | TGC | TAC | ACG | GCG | CAC | TTC | AAC | ACC | TAC | CTG | GTT | CTC | ATC | 1161 |
| Tyr | Cys | Ile | Cys | Tyr | Thr | Ala | His | Phe | Asn | Thr | Tyr | Leu | Val | Leu | Ile | |
| | | 275 | | | | | 280 | | | | | 285 | | | | |

```
ATG TGC AAC TCT GTC ATC GAC CCC CTC ATC TAC GCC TTC CGC AGC CTG        1209
Met Cys Asn Ser Val Ile Asp Pro Leu Ile Tyr Ala Phe Arg Ser Leu
    290                 295                 300

GAG CTG CGA AAC ACC TTC AAG GAG ATT CTC TGC GGT TGC AAT GGC ATG        1257
Glu Leu Arg Asn Thr Phe Lys Glu Ile Leu Cys Gly Cys Asn Gly Met
305                 310                 315                 320

AAC GTG GGC TAGGAACCCC CGAGGAGGTG TTCCACGGCT AGCCAAGAGA                1306
Asn Val Gly

GAAAAGCAAT GCTCAGGTGA GACACAGAAG GG                                    1338
```

(2) INFORMATION FOR SEQ ID NO: 4:

(i) SEQUENCE CHARACTERISTICS:
        (A) LENGTH: 323 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Asn Ser Ser Cys Cys Pro Ser Ser Tyr Pro Thr Leu Pro Asn
 1               5                  10                  15

Leu Ser Gln His Pro Ala Ala Pro Ser Ala Ser Asn Arg Ser Gly Ser
                20                  25                  30

Gly Phe Cys Glu Gln Val Phe Ile Lys Pro Glu Val Phe Leu Ala Leu
            35                  40                  45

Gly Ile Val Ser Leu Met Glu Asn Ile Leu Val Ile Leu Ala Val Val
        50                  55                  60

Arg Asn Gly Asn Leu His Ser Pro Met Tyr Phe Phe Leu Leu Ser Leu
65                  70                  75                  80

Leu Gln Ala Asp Met Leu Val Ser Leu Ser Asn Ser Leu Glu Thr Ile
                85                  90                  95

Met Ile Val Val Ile Asn Ser Asp Ser Leu Thr Leu Glu Asp Gln Phe
            100                 105                 110

Ile Gln His Met Asp Asn Ile Phe Asp Ser Met Ile Cys Ile Ser Leu
        115                 120                 125

Val Ala Ser Ile Cys Asn Leu Leu Ala Ile Ala Val Asp Arg Tyr Val
    130                 135                 140

Thr Ile Phe Tyr Ala Leu Arg Tyr His Ser Ile Met Thr Val Arg Lys
145                 150                 155                 160

Ala Leu Ser Leu Ile Val Ala Ile Trp Val Cys Gly Ile Cys Gly
                165                 170                 175

Val Met Phe Ile Val Tyr Ser Glu Ser Lys Met Val Ile Val Cys Leu
            180                 185                 190

Ile Thr Met Phe Phe Ala Met Val Leu Leu Met Gly Thr Leu Tyr Ile
        195                 200                 205

His Met Phe Leu Phe Ala Arg Leu His Val Gln Arg Ile Ala Ala Leu
    210                 215                 220

Pro Pro Ala Asp Gly Val Ala Pro Gln Gln His Ser Cys Met Lys Gly
225                 230                 235                 240

Ala Val Thr Ile Thr Ile Leu Leu Gly Val Phe Ile Phe Cys Trp Ala
                245                 250                 255

Pro Phe Phe Leu His Leu Val Leu Ile Ile Thr Cys Pro Thr Asn Pro
            260                 265                 270

Tyr Cys Ile Cys Tyr Thr Ala His Phe Asn Thr Tyr Leu Val Leu Ile
        275                 280                 285
```

-continued

```
Met Cys Asn Ser Val Ile Asp Pro Leu Ile Tyr Ala Phe Arg Ser Leu
    290                 295                 300

Glu Leu Arg Asn Thr Phe Lys Glu Ile Leu Cys Gly Cys Asn Gly Met
305                 310                 315                 320

Asn Val Gly
```

We claim:

1. An isolated and purified melanocortin receptor having a predicted molecular weight of about 35,700 daltons and an amino acid sequence identified by SEQ ID No. 4.

2. A cell membrane preparation comprising a melanocortin receptor having an amino acid sequence identified by SEQ ID No. 4, produced by a cell that expresses a recombinant expression vector encoding said melanocortin receptor, wherein said cell does not endogenously produce said melanocortin receptor.

* * * * *